United States Patent
Chen et al.

(10) Patent No.: US 9,216,893 B2
(45) Date of Patent: Dec. 22, 2015

(54) FEED SYSTEMS WITH CONSTANT PRESSURES

(71) Applicants: Kuang-Yung Chen, Taoyuan County (TW); Chun-Ming Lai, Taoyuan County (TW); Chun-Liang Yang, Taoyuan County (TW)

(72) Inventors: Kuang-Yung Chen, Taoyuan County (TW); Chun-Ming Lai, Taoyuan County (TW); Chun-Liang Yang, Taoyuan County (TW)

( * ) Notice: Subject to any disclaimer, the term of this patent is extended or adjusted under 35 U.S.C. 154(b) by 0 days.

(21) Appl. No.: 14/221,628

(22) Filed: Mar. 21, 2014

(65) Prior Publication Data

US 2015/0114990 A1    Apr. 30, 2015

(30) Foreign Application Priority Data

Oct. 25, 2013   (TW) .............................. 102219954 U

(51) Int. Cl.
| | |
|---|---|
| *B67D 7/36* | (2010.01) |
| *A61M 5/00* | (2006.01) |
| *B67D 7/02* | (2010.01) |
| *B67D 7/72* | (2010.01) |
| *B67D 7/16* | (2010.01) |
| *B67D 7/42* | (2010.01) |
| *B05C 11/10* | (2006.01) |

(52) U.S. Cl.
CPC .. *B67D 7/36* (2013.01); *A61M 5/00* (2013.01); *B05C 11/1036* (2013.01); *B67D 7/0266* (2013.01); *B67D 7/72* (2013.01); *B05C 11/1002* (2013.01); *B67D 7/16* (2013.01); *B67D 7/42* (2013.01)

(58) Field of Classification Search
CPC .............. B67D 7/16; B67D 7/36; B67D 7/42; B67D 7/72; B67D 7/0266; B05C 11/1002; B05C 11/1036; A61M 5/00
USPC ............................. 222/55, 52, 14, 53, 71, 152
See application file for complete search history.

(56) References Cited

U.S. PATENT DOCUMENTS

| | | | | |
|---|---|---|---|---|
| 3,950,762 | A * | 4/1976 | Anderka ...................... 346/140.1 |
| 4,989,756 | A * | 2/1991 | Kagamihara et al. ........... 222/55 |
| 5,199,607 | A * | 4/1993 | Shimano ......................... 222/55 |
| 5,449,545 | A * | 9/1995 | Toya et al. ..................... 428/138 |
| 5,499,545 | A * | 3/1996 | Kimura et al. .............. 73/864.18 |
| 6,213,354 | B1 * | 4/2001 | Kay .............................. 222/420 |
| 6,371,331 | B1 * | 4/2002 | Gohde et al. .................... 222/55 |

\* cited by examiner

*Primary Examiner* — Frederick C Nicolas
(74) *Attorney, Agent, or Firm* — WPAT, PC; Justin King

(57) ABSTRACT

The present invention discloses a feed system with a constant pressure. The feed system comprises a feed container which has a depressurize port mounted on its top, a intake port mounted at its side, and a feed port mounted on its bottom, contains a liquid material being a medicine or a liquid glue mixture; a intake structure which comprises a throttle pipeline and a throttle valve; a opening controller which connects to the throttle valve and the pressure sensor, for controlling the intake structure. The advantage of the feed system is to control the feed flow rate so as to maintain a constant during the feed process, particularly in the hybrid feed system. By steadily controlling the output flow rate, the mixed proportion is controlled to generate the product with the stable quality when two or more liquid materials must be mixed according to the specific proportion.

8 Claims, 2 Drawing Sheets

FEED SYSTEMS WITH CONSTANT PRESSURES

BACKGROUND OF THE INVENTION

1. Field of the Invention

This invention generally relates to a feed system, and more particularly, to a feed system with a constant pressure. The feed system being a liquid feed system with follow-up pressure is used in the medicament fill, the industrial dispensing, etc.

2. Description of the Prior Art

The automatic feed system is a very common application in the food industry, the pharmaceutical industry, etc. In conventional technology, the automatic feed system directly provides a steady air pressure to the top of the feed container to press out the liquid in the feed container download. This way will generate the difference of liquid level based on the liquid is effused slowly and orderly, as shown in FIG. 1A and 1B. Because the air weight is much smaller than the liquid weight, the output pressure value will be changed. Hence, the pressure located at the feed port is reduced slowly, and it will result in the variable of the feed flow rate.

In actual application, when two or more liquid materials must be mixed according to the specific proportion, it will cause that the entire chemical composition is changed and generates a failure product if the flow rate of one of the liquid materials is changed. Thereby, if a technology of steadily controlling the flow rate is provided, the output pressure value will not changed with the liquid level change so as to generate the product with the stable quality.

For the reason that the conventional feed system could not provide a constant pressure for generating products with steady quality, a need has arisen to propose a novel scheme that may adaptively provide a constant pressure and steadily control the output flow rate so as to generate the product with the stable quality.

SUMMARY OF THE INVENTION

In view of the foregoing, it is an object of the present invention to provide a feed system with a constant pressure, and the advantage of the feed system is to control the feed flow rate so as to maintain a constant during the feed process, particularly in the hybrid feed system. The advantage of the present invention is significant, when two or more liquid materials must be mixed according to the specific proportion, it will cause that the entire chemical composition is changed and generates a failure product if the flow rate of one of the liquid materials is changed. Nevertheless, in the present invention, by steadily controlling the output flow rate, the mixed proportion is controlled to generate the product with the stable quality.

Based on the abovementioned objectives of the present invention, a feed system with a constant pressure is disclosed according to one embodiment of the present invention. The feed system with a constant pressure comprises a feed container, which has a depressurize port mounted on its top, a intake port mounted at its side, and a feed port mounted on its bottom, contains a liquid material being a medicine or a liquid glue mixture, wherein a flow rate of the liquid material is adjusted by controlling a pressure pressed into the feed port; a pressure sensor, being located at the feed port; a intake structure, which comprises a throttle pipeline and a throttle valve, wherein the throttle pipeline is connected to the feed container, and an opening size of the throttle valve located in the throttle pipeline is controlled to adjust the liquid flow rate; a opening controller, which connects to the throttle valve and the pressure sensor, for controlling the intake structure, wherein the opening controller reads a pressure value of the pressure sensor, and then controls an opening size of the throttle valve to maintain the pressure value of the pressure sensor unchanged after logically comparing, and thereby, the liquid discharge velocity from the feed container keeps a constant velocity.

The feed system with the constant pressure further comprises: a depressurization structure, which comprises a depressurization pipeline, a depressurization valve and a drive source; wherein the depressurization valve is mounted in the depressurization pipeline, and the drive source is connected to the depressurization valve so as to control the switch of the depressurization valve; wherein the depressurization structure is set outside the feed container, and the depressurization pipeline is serially connected to the depressurization port of the feed container, and the depressurization valve of the depressurization pipeline controls the switch of the depressurization port by the drive source so as to discharge the pressure in the feed container.

BRIEF DESCRIPTION OF THE DRAWINGS

The accompanying drawings incorporated in and forming a part of the specification illustrate several aspects of the present invention, and together with the description serve to explain the principles of the disclosure. In the drawings.

DETAILED DESCRIPTION OF THE PREFERRED EMBODIMENTS

Some embodiments of the present invention will now be described in greater detail. Nevertheless, it should be noted that the present invention can be practiced in a wide range of other embodiments besides those explicitly described, and the scope of the present invention is expressly not limited except as specified in the accompanying claims.

Moreover, some irrelevant details are not drawn in order to make the illustrations concise and to provide a clear description for easily understanding the present invention.

Figure 1A:
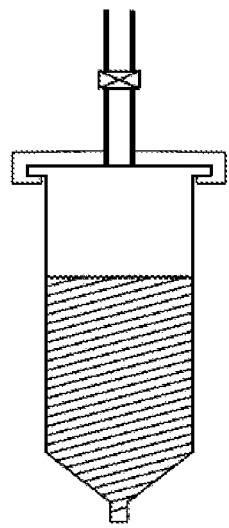
FIG. 1A shows a schematic diagram of the conventional feed container before feeding.
Figure 1B:
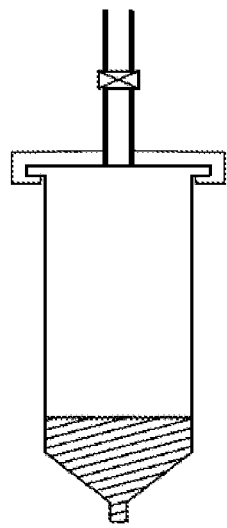
FIG. 1B shows a schematic diagram of the conventional feed container during the feeding.
Figure 2:
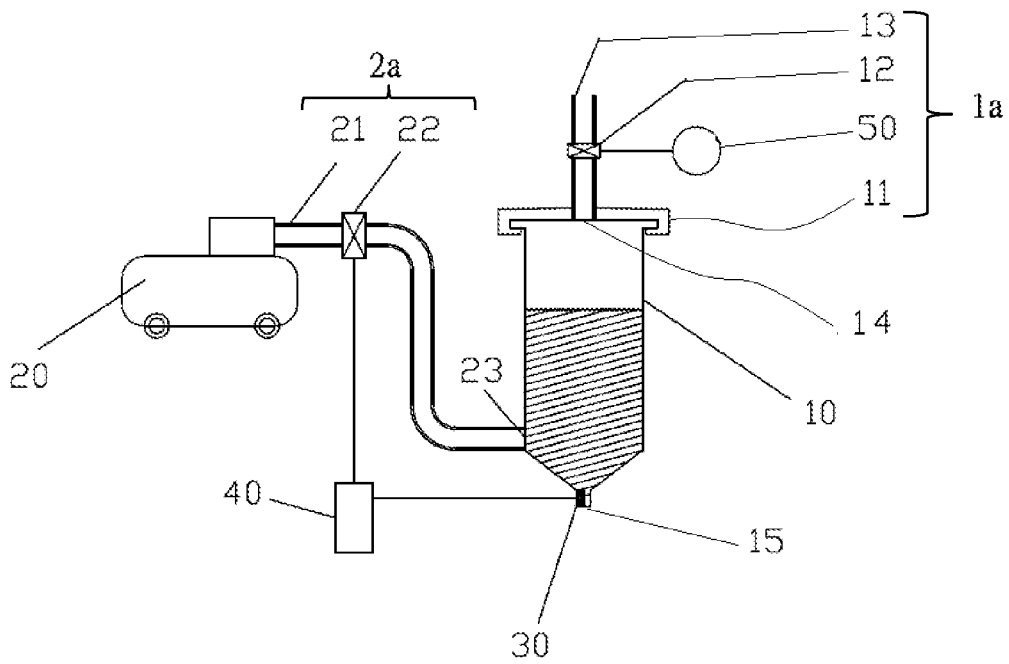
FIG. 2 shows a schematic diagram illustrating the structure according to one embodiment of the present invention.

Referring to FIG. 2, which illustrates a feed system with a constant pressure according to one embodiment of the present invention. The feed system comprises a feed container 10, an intake structure 2a, a pressure sensor 30 and an opening controller 40.

The feed container 10 has a depressurize port 14 mounted on its top, an intake port 23 mounted at its side, and a feed port 15 mounted on its bottom. The feed container 10 contains a liquid material, for example, a medicine or a liquid glue mixture. There is an empty space located on the above of the liquid material in the feed container 10 for containing the air. By pressing the pressure into the intake port 23, the liquid material is pushed out so as to effuse from the feed port 15. A pressure sensor 30 is located at the feed port 15 for sensing the above pressure of the feed port 15 and the above pressure is a total pressure being the result of adding the pressure from the liquid material and the air. Perfectly, the feed container 10 further comprises a seal cap 11 serially connected to the feed container 10 for sealing the feed container 10 and preventing the external environment pressure to effect the feed container 10.

The intake structure 2a, which comprises a throttle pipeline 21, throttle valve 22. The throttle pipeline 21 is connected to the feed container 10 through the intake port 23, and the throttle valve 22 mounted on the throttle pipeline 21 is used to control the flow rate of the liquid material. The throttle valve 22 further comprises a drive source used to drive the throttle valve 22. The feed system of the present invention utilizes an air compressor 20 to press the air pressure into the feed container 10 through the intake port 23. The location of the intake port 23 is located near the bottom of the feed port 10, rather than located on the top of the liquid material. This design allows the pressure of the feed port not change with level condition change of the liquid surface so as to affect the feed flow rate.

The opening controller 40 electrically coupling to the throttle valve 22 and the pressure sensor 30. The opening controller 40 may read the pressure value of the pressure sensor 30, and then control the opening size of the throttle valve 22 to maintain the pressure value of the pressure sensor 30 unchanged after logically comparing. Thereby, the liquid discharge velocity from the feed container 10 may keep a constant velocity. The electrical coupling may the wire connection or the wireless connection.

The depressurization structure 1a comprises a depressurization pipeline 13, a depressurization valve 12, a seal cap 11 and a drive source 50. Specifically, the depressurization valve 12 is mounted in the depressurization pipeline 13, and the drive source 50 is connected to the depressurization valve 12 so as to control the switch of the depressurization valve 12. The depressurization structure is set outside the feed container 10, and the depressurization pipeline 13 is serially connected to the depressurization port 14 of the feed container 10, and the depressurization valve 12 of the depressurization pipeline 13 controls the switch of the depressurization port 14 by the drive source 50 so as to discharge the pressure in the feed container 10. The drive source 50 is driven by the engine or the air pressure. Perfectly, the depressurization valve 12 is connected to the seal cap 11, and there is a hole located on the seal cap 11 for allowing the depressurization pipeline 13 connecting to the seal cap 11 through the hole.

In the entire feed process, the liquid material is effused slowly and orderly due to the weight difference between the air and liquid. As the liquid level dropped slowly, the pressure located at the feed port is decreased so as to affect the feed flow rate. However, the feed system of the present invention may utilize the intake structure to compensate the pressure difference because of the level of liquid dropped. The opening controller 40 may continuously adjust the output pressure to maintain a constant pressure during the feed process so as to achieve the purpose of controlling flow rate steady.

The advantage of the present invention is to control the feed flow rate so as to maintain a constant during the feed process, particularly in the hybrid feed system. The advantage of the present invention is significant, when two or more liquid materials must be mixed according to the specific proportion, it will cause that the entire chemical composition is changed and generates a failure product if the flow rate of one of the liquid materials is changed. Nevertheless, in the present invention, by steadily controlling the output flow rate, the mixed proportion is controlled to generate the product with the stable quality.

Figure 3:
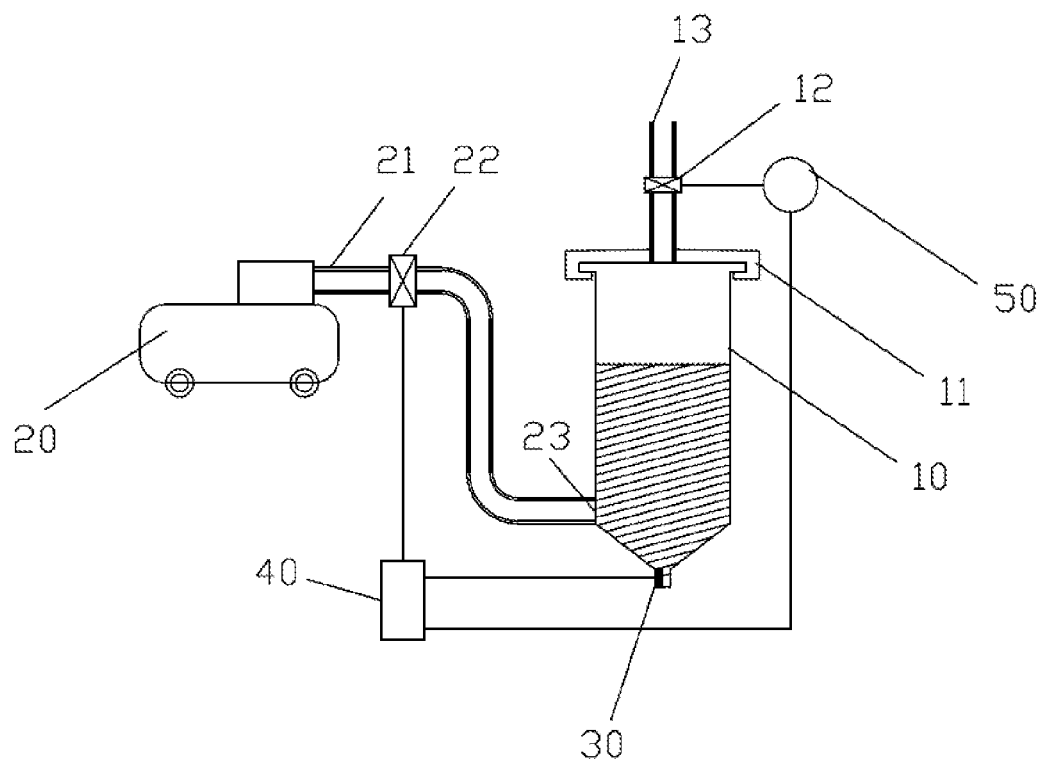
FIG. 3 shows a schematic diagram illustrating the structure according to another embodiment of the present invention.

As mentioned description, the feed system with the constant pressure disclosed by the present invention also may be a feed system with the variable pressure, as shown in FIG. 3.

Expect that the feed system of the present invention comprises the abovementioned elements, the opening controller 40 is connected to the drive source 50 of the depressurization valve 22, meanwhile may control the opening sizes of the throttle valve 22 and the depressurization valve 12. Thereby, the air pressure located on the top of the liquid material in the feed container 10 may be adjusted according to the actual requirement.

Figure 4:
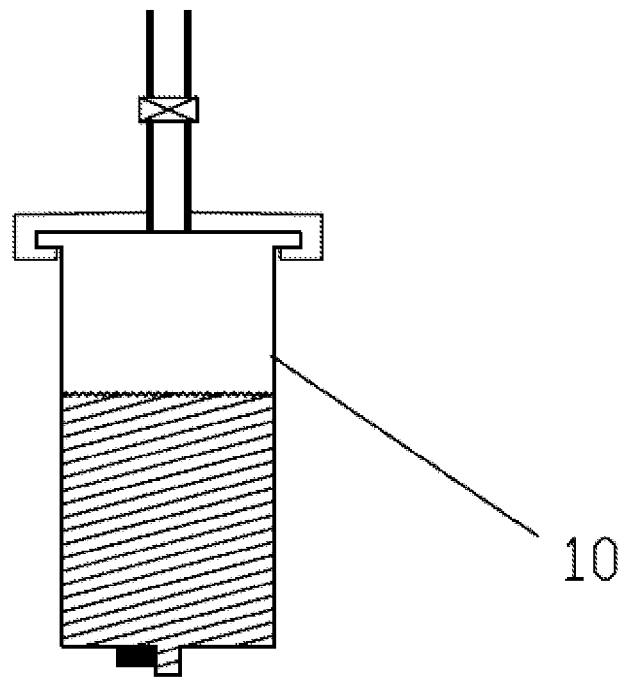
FIG. 4 shows a schematic diagram illustrating the element structure according to one embodiment of the present invention.

The feed container in the present invention may be any types or shapes, and therefore, the shape consideration change falls within the scope of the included claims. As shown in FIG. 4, the feed container 10 is a flat shape.

Although specific embodiments have been illustrated and described, it will be obvious to those skilled in the art that various modifications may be made without departing from what is intended to be limited solely by the appended claims.

What is claimed is:

1. A feed system with a constant pressure, comprising:
   a feed container, containing a liquid material being a medicine or a liquid glue mixture;
   a depressurize port positioned above said feed container and mounting on said feed container;
   an intake port positioned next to said feed container and mounted on said feed container;
   a feed port position below said feed container and mounted on said feed container, wherein a flow rate of the liquid material is adjusted by controlling a pressure pressed into the feed port;
   a pressure sensor, being located at the feed port;
   an intake structure, comprising a throttle pipeline and a throttle valve, wherein the throttle pipeline is connected to the feed container, and an opening size of the throttle valve located in the throttle pipeline is controlled to adjust the liquid flow rate; and
   an opening controller, connecting to the throttle valve and the pressure sensor, for controlling the intake structure, wherein the opening controller reads a pressure value of the pressure sensor, and then controls an opening size of the throttle valve to maintain the pressure value of the pressure sensor unchanged after logically comparing, and thereby, a liquid discharge velocity from the feed container keeps a constant velocity.

2. The feed system according to claim 1, further comprising:
   a depressurization structure, comprising a depressurization pipeline, a depressurization valve, and a drive source;
   wherein the depressurization valve is mounted in the depressurization pipeline, and the drive source is connected to the depressurization valve so as to control the switch of the depressurization valve;
   wherein the depressurization structure is set outside the feed container, and the depressurization pipeline is serially connected to the depressurization port of the feed container, and the depressurization valve of the depressurization pipeline controls the switch of the depressurization port by the drive source so as to discharge the pressure in the feed container.

3. The feed system according to claim 1, wherein the pressure sensor senses an above pressure of the feed port and the above pressure is a total pressure being the result of adding pressures from the liquid material and an air.

4. The feed system according to claim 1, wherein the opening controller electrically coupling to the throttle valve and the pressure sensor, and the opening controller reads the pressure value of the pressure sensor, and then controls the opening size of the throttle valve to maintain the pressure value of the pressure sensor unchanged after logically comparing, and thereby, the liquid discharge velocity from the feed container keeps a constant velocity, wherein an electrical coupling is a wire connection or a wireless connection.

5. The feed system according to claim 1, wherein the depressurization structure further comprises a seal cap, and the depressurization valve is connected to the seal cap, and there is a hole located on the seal cap for allowing the depressurization pipeline connecting to the seal cap through the hole.

6. The feed system according to claim 1, wherein the intake port is located near a bottom of the feed port and below a top level of the liquid material.

7. The feed system according to claim 1, wherein the feed system being a liquid feed system with follow-up pressure is used in a medicament fill and an industrial dispensing.

8. The feed system according to claim 2, wherein the opening controller is connected to the drive source of the depressurization valve, wherein said opening controller controls a air pressure above the liquid material in the feed container controlling said throttle valve and said depressurization valve.

\* \* \* \* \*